(12) United States Patent
Zeller et al.

(10) Patent No.: US 11,998,309 B2
(45) Date of Patent: Jun. 4, 2024

(54) MAGNETIC RESONANCE FACILITY OPERATION

(71) Applicant: Siemens Healthcare GmbH, Erlangen (DE)

(72) Inventors: Mario Zeller, Erlangen (DE); Michael Köhler, Nuremberg (DE); Dominik Paul, Bubenreuth (DE)

(73) Assignee: Siemens Healthineers AG, Forchheim (DE)

( * ) Notice: Subject to any disclaimer, the term of this patent is extended or adjusted under 35 U.S.C. 154(b) by 0 days.

(21) Appl. No.: 18/129,221

(22) Filed: Mar. 31, 2023

(65) Prior Publication Data
US 2023/0309850 A1    Oct. 5, 2023

(30) Foreign Application Priority Data
Apr. 1, 2022   (DE) .................. 10 2022 203 251.9

(51) Int. Cl.
*G01V 3/00* (2006.01)
*A61B 5/055* (2006.01)

(52) U.S. Cl.
CPC .... *A61B 5/055* (2013.01); *G06T 2207/10088* (2013.01)

(58) Field of Classification Search
CPC ............. G01R 33/3415; G01R 33/543; G01R 33/5659; G01R 33/36; A61B 5/055
(Continued)

(56) References Cited

U.S. PATENT DOCUMENTS

2016/0171670 A1*  6/2016  Koehler ............. G01R 33/5608
                                                            382/131
2019/0018092 A1   1/2019  Ookawa et al.
(Continued)

FOREIGN PATENT DOCUMENTS

CN   110398705 A    11/2019
CN   113625211 A    11/2021
(Continued)

OTHER PUBLICATIONS

Zhao X. et al. "Impact of Gradient Imperfections on Bone Water Quantification with UTE MRI" Magnetic Resonance in Medicine 84.4 (2020): 2034-2047.
(Continued)

*Primary Examiner* — Walter L Lindsay, Jr.
*Assistant Examiner* — Frederick Wenderoth
(74) *Attorney, Agent, or Firm* — Banner & Witcoff Ltd.

(57) ABSTRACT

A method for operating a magnetic resonance facility in which a measurement gradient pulse is used to record magnetic resonance signals for sampling k-space along a trajectory section. The recorded magnetic resonance signals are assigned to k-space points using a shape function describing the time profile of the measurement gradient pulse. To correct deviations of the real time profile of the measurement gradient pulse from an assumed target profile, a first correction measurement is performed to ascertain first magnetic resonance signals of the trajectory section. A second correction measurement is then performed using a reference sampling pattern or a reference gradient pulse with fewer deviations from an assigned reference target profile. If a deviation criterion is met, a correction function for the shape function is ascertained by aligning the first and second magnetic resonance signals to one another, providing correction information to be used in an imaging measurement.

16 Claims, 5 Drawing Sheets

(58) Field of Classification Search
USPC .......................................................... 324/309
See application file for complete search history.

(56) References Cited

U.S. PATENT DOCUMENTS

| | | |
|---|---|---|
| 2019/0324103 A1 | 10/2019 | Shi et al. |
| 2020/0132795 A1 | 4/2020 | Beck et al. |
| 2020/0249303 A1 | 8/2020 | Liebig et al. |
| 2020/0400770 A1 | 12/2020 | Köhler |
| 2021/0215780 A1 | 7/2021 | Grodzki |
| 2021/0349168 A1 | 11/2021 | Feiweier |
| 2022/0026512 A1 | 1/2022 | Kettinger et al. |
| 2022/0043092 A1 | 2/2022 | Stich et al. |

FOREIGN PATENT DOCUMENTS

| | | |
|---|---|---|
| CN | 113970715 A | 1/2022 |
| DE | 102018218471 B3 | 2/2020 |
| DE | 102019201385 B3 | 7/2020 |
| DE | 102019209079 A1 | 12/2020 |
| DE | 102020200389 A1 | 7/2021 |
| DE | 102020209787 A1 | 2/2022 |

OTHER PUBLICATIONS

Ma C. et al. "A New Eddy-Current Compensation Method in MRI" PIERS online 3.6 (2007): 874-878.

\* cited by examiner

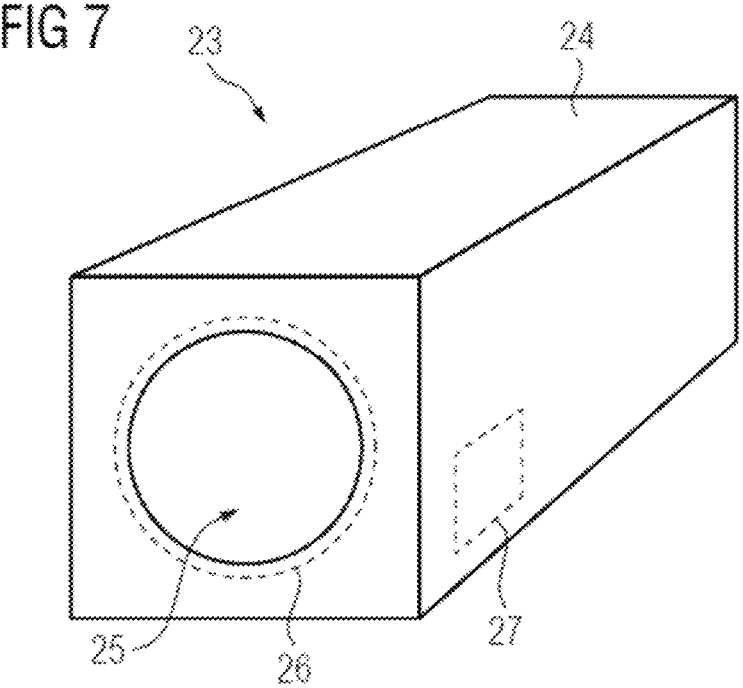
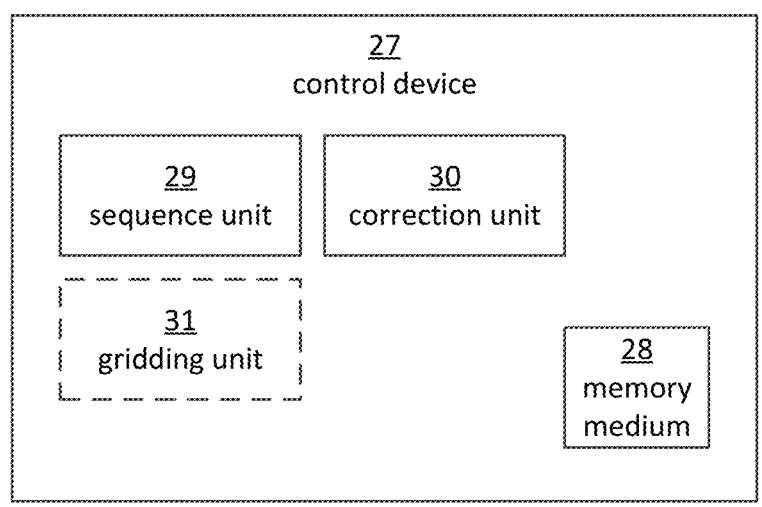

MAGNETIC RESONANCE FACILITY OPERATION

TECHNICAL FIELD

The disclosed subject matter relates to a method for operating a magnetic resonance facility in which a measurement gradient pulse is used to record magnetic resonance signals for sampling the k-space along a trajectory section, wherein the measurement of the magnetic resonance signals takes place at recording times forming a measurement sampling pattern in a recording time window during the measurement gradient pulse and a shape function describing the time profile of the measurement gradient pulse is used to assign recorded magnetic resonance signals to k-space points. In addition, the disclosed subject matter relates to a magnetic resonance facility, a computer program and an electronically readable data carrier.

BACKGROUND

In magnetic resonance imaging, it is known to achieve spatial encoding of recorded magnetic resonance signals by gradient pulses generated by a gradient coil array. During the application of a gradient pulse, depending on its amplitude, a moment is introduced that influences the k-space position. Herein, the path traveled in k-space during a magnetic resonance measurement is also referred to as the k-space trajectory. In this context, it is known also to have at least one measurement gradient pulse (often also referred to as a readout gradient pulse) present during the actual recording time window; in the simplest case, this has a constant amplitude during the recording time window, meaning that k-space is traversed at uniform speed in the direction of the applied gradient (k-space line). However, more complex gradient shapes have been also been proposed in the prior art, for example in the case of spiral sampling and/or as a sinusoidal gradient.

In another example of the prior art, it has, for example, been proposed within the context of echo planar imaging (EPI) that faster recording of all required magnetic resonance signals be achieved in that the recording time window also already comprises the ramps of a trapezoidal gradient. This is referred to as ramp sampling. In this way, magnetic resonance signals are recorded not only in the constant range of the trapezoidal measurement gradient pulse, but also during its rising and falling edges. However, with recording times that are equidistant in time, this results in non-linear, i.e., non-Cartesian, sampling of the k-space since there is higher sampling density in k-space for the lowest and highest k-space values due to the gradient pulse that is still rising or falling again. Due to the non-equidistant, and thus non-linear, k-space sampling, image acquisition by means of a simple Fourier transform is not directly possible, instead a further pre-processing step is required, namely a correction of the k-space, for example by means of convolution gridding. In such a pre-processing step, re-gridding takes place in which the non-linear k-space points are converted to a Cartesian sampling grid. Ideally, the assignment of magnetic resonance signals sampled at recording times to k-space positions on which the gridding is based can take place by means of the following equations:

$$G(t) = \begin{cases} S_R \cdot (t + t_2) & -t_2 \leq t < -t_1 \\ G_x & -t_1 \leq t < t_1 \\ S_R \cdot (t_2 - t) & t_1 \leq t < t_2 \end{cases} \quad (1)$$

-continued
$$k_x(t) = \frac{\gamma}{2} \begin{cases} S_R \cdot (t + t_2)^2 - G_x \cdot (t_1 + t_2) & -t_2 \leq t < -t_1 \\ 2 G_x t & -t_1 \leq t < t_1 \\ 2 G_x t_1 + 2 S_R t_2 \cdot (t - t_1) + S_R \cdot (t_1^2 - t^2) & t_1 \leq t < t_2 \end{cases} \quad (2)$$

Herein, $G(t)$ is the trapezoidal gradient profile, $k_x(t)$ is the k-space position at the time t of the measurement gradient pulse and results from integration after t. Due to the blipping gradient pulses (blips) played out simultaneously in the phase-encoding direction during echo planar imaging, $-t_2$ and $t_2$ are not usually at the beginning and end of the ramp, but at slightly later or earlier times. These edge values mark the boundaries of the recording time window. $-t_1$ and $t_1$ describe the beginning and end of the ramp. $S_R$ is the slope of the ramp, $G_x$ is the amplitude of the plateau.

As can be seen from the equations (1) and (2) shown, with such pre-processing steps, a specific ideal gradient shape is assumed for the conversion of the magnetic resonance signals to a Cartesian sampling grid, in the case of ramp sampling, for example, an ideal trapezoidal profile. Even when recording within a plateau of the measurement gradient pulse, a corresponding assumption is made, namely that a constant amplitude of the measurement gradient pulse was present and thus there is inevitably a Cartesian sampling grid. However, in reality, such an assumption is not always true. Here, time delays, not fully compensated eddy currents and other dynamic effects can have the result that the measurement gradient pulse that is played out does not correspond to the ideal shape. If a constant gradient amplitude is assumed or if a correction of the k-space with the ideal time profile of the measurement gradient pulse is performed in the pre-processing step, artifacts can occur in the reconstructed image result, for example edge overemphasis. In the case of trapezoidal gradients, it is, for example, known that the plateau is not reached until a later time with the rising ramp and/or that, at least at the beginning of the plateau, fluctuations of the gradient amplitude still occur and, if the profile is assumed to be constant, these can also lead to artifacts.

For imaging techniques in which trapezoidal measurement gradient pulses are not used, but other time profiles are employed or also in so-called spiral imaging in which a spiral k-space trajectory is traversed by time-varying measurement gradients on two axes, a gridding pre-processing step is also applied to convert the measured magnetic resonance signals into a Cartesian sampling grid in k-space, i.e., equidistant sampling along Cartesian axes. In this case, once again, if the assumed shape function corresponding to equation (1) for such cases does not correspond to reality, this can result in faulty pre-processing and thus in artifacts.

In the case of significant differences between the assumed target profile and the actual time profile of the measurement gradient pulse, even with conventional imaging, i.e., when the recording time window for the magnetic resonance signals is only set during the plateau of the measurement gradient pulse, incorrect assumptions may be made regarding the assignment of magnetic resonance signals to k-space points, meaning that artifacts can occur. This primarily relates to sampling points recorded at the beginning of the gradient plateau, since practice has shown that particularly large discrepancies between the assumed and actual profile of the measurement gradient pulse can occur in this time range. Usually, no gridding is performed in such cases since the data points are nominally recorded in a Cartesian grid. Nevertheless, even in such cases, a deviation from the real gradient shape, i.e., the real time profile, can result in artifacts, for example ringing artifacts, ghosting artifacts or elevation artifacts in the area of the edges and boundaries of structures.

To solve or at least reduce these problems, it has been proposed that eddy current compensation be performed in current magnetic resonance facilities. This is based on a measurement of the eddy currents of the respective magnetic resonance facility. In this case, the eddy current effects are compensated during the course of so-called "pre-emphasis" when the gradient pulses are played out. However, there are technical limits with regard to such eddy current compensation, for example with regard to resolvable dynamic behavior. Furthermore, eddy current compensation is usually based on measurements that represent averaging over a certain spatial range. In addition, known compensation methods only correct eddy current effects of linear profiles which can be compensated by playing out additional gradient pulses. Specifically, in this way, for example, the "average" gradient-like eddy current effect is compensated by an additional x-gradient pulse in the x-direction. In this case, spatial dependence in the z- or y-direction is not usually taken into account. In reality, these limitations mean that, despite the application of eddy current compensation, imperfections can still occur in the time profile of the measurement gradient pulse that is played out.

It has also been suggested in the prior art that deviations of the assumed time profile of the measurement gradient pulse from the real time profile of the measurement gradient pulse also be measured by means of in particular permanently installed magnetic field sensors (so-called "field probes") and/or using the gradient impulse response function (GIRF) with corresponding temporal resolution. However, the use of magnetic field sensors is expensive, the sensors age and have to be renewed regularly. Furthermore, in some circumstances, it may be necessary to redesign the magnetic resonance sequences to enable signal emission at the Larmor frequency of the magnetic field sensors. GIRF measurements, on the other hand, are time-consuming and have to be repeated at regular intervals, meaning that no correction for temporary effects can take place.

An article by C. Ma and X. H. Jiang, "A New Eddy-current Compensation Method in MRI", PIERS Online, No. 6 (2007), pages 874-878, proposes the use of a mathematical model to calculate the non-uniform sampling trajectory in k-space distorted by eddy currents in order to ascertain the correct positions of the measured k-space points, whereupon gridding can be performed. The model can also calculate induced additional phases due to zero-order eddy currents in order to correct the phase of the magnetic resonance signal before gridding construction.

SUMMARY

The disclosed subject matter is based on an object of improving the quality of magnetic resonance image data with regard to imperfections in the measurement gradient shape.

This object is achieved by a method, a magnetic resonance facility, a computer program and an electronically readable data carrier with the features of the corresponding independent claims. Advantageous embodiments result from the subclaims.

According to the disclosed subject matter, it is provided in a method of the type mentioned in the introduction that, to ascertain correction information relating to deviations of the real time profile of the measurement gradient pulse from an assumed target profile of the measurement gradient pulse in the recording time window to be used in an imaging measurement in the course of an ascertaining process which in particular takes place outside the imaging measurement, a first correction measurement for ascertaining first magnetic resonance signals of the trajectory section is performed by applying the measurement sampling pattern to the measurement gradient pulse under predetermined measurement conditions, a second correction measurement for ascertaining second magnetic resonance signals of the trajectory section under the predetermined measurement conditions is performed using a reference sampling pattern at gradient conditions of the measurement gradient pulse and/ or a reference gradient pulse, wherein the gradient conditions are expected to have fewer deviations from an assigned reference target profile, when a deviation criterion comparing the frequency of first and second magnetic resonance signals is satisfied, a correction function for the shape function is ascertained as correction information by aligning of the first and second magnetic resonance signals to one another.

Herein, the deviation criterion checks whether the deviation between the first and the second magnetic resonance signals is sufficiently large to justify ascertaining correction information. For example, it is possible to check whether the deviation, possibly described by at least one deviation measure, exceeds a threshold value. If the deviation criterion is not satisfied, the correction information may indicate that no correction is required. However, if the correction information contains a correction function for the shape function, by means of which measured magnetic resonance signals are assigned to k-space points, the assignment of the magnetic resonance signals to k-space points can be corrected on the basis of the correction information in at least one subsequent imaging measurement.

Therefore, the disclosed subject matter proposes a procedure for determining the actual k-space trajectory k(t). This can be applied to correct the assignment of measurement data, namely magnetic resonance signals, to k-space points in the case of imperfections in the time profile of measurement gradient pulses (readout gradient pulses). Herein, there is a wide range of applications, for example in ramp sampling, in measurements with time-varying measurement gradient pulses (for example with sinusoidal readout gradients or spiral imaging) and/or in the correction assignment of magnetic resonance signals recorded at recording times, which in the case of trapezoidal measurement gradient pulses were recorded shortly after the beginning of the plateau, i.e., at recording times at which there are significant deviations between the target profile and the actual time profile of the measurement gradient pulse.

Herein, the fundamental idea of the present disclosed subject matter is to perform two measurements under the same measurement conditions (except for the gradient conditions), in particular therefore with the same object, once with the sampling pattern and measurement gradient pulse also provided for the imaging measurement, for example therefore with ramp sampling, and once with a reference recording in which robust dimensioning of the measurement gradient is used, and, to be precise, in such a way that there are no imperfections, or only minor imperfections, in the gradient profile during the recording time window. Therefore, during the first correction measurement, it should be assumed that the k-space positions of the measured magnetic resonance signals are distorted by imperfections in the gradient shape of the measurement gradient pulse, i.e., deviations of the time profile from the shape function. With the second correction measurement (reference measurement), this is not the case or only negligibly the case. Herein, in particular a recording time window in which a constant measurement gradient is present, for example during the plateau of a trapezoidal measurement gradient pulse or reference gradient pulse, is suitable for the second correction measurement.

In other words, the recording time window of the reference sampling pattern particularly preferably lies entirely within a gradient plateau, particularly advantageously preferably spaced apart from the beginning of the gradient plateau by at least one predetermined delay time. Therefore, a second correction measurement, in which some time, namely the delay time, elapses between the beginning of the gradient plateau and the beginning of the recording time window is particularly advantageous. Herein, the delay time is in particular selected such that in particular eddy current-induced disturbances leading to the deviation have decayed. For example, the delay time can be between 100 and 500 μs. Herein, it should be noted that the (preferably Cartesian) measurement is particularly preferably within a plateau, but does not necessarily represent the only possible variant since other robust gradient pulse sections or, more generally, gradient conditions are also conceivable; for example, those established using the methods already discussed relating to the prior art.

Herein, the first and the second correction measurement record first and second magnetic resonance signals of the trajectory section, i.e., more precisely of the k-space region covered by the trajectory section, which, however, as will be explained below, does not have to be sampled completely as long as the first and the second correction measurement refer to the same subregion. In particular, the shape endowed by the measurement sampling pattern in combination with the measurement gradient pulse can be shifted within k-space by suitable prephasing, meaning that in particular the passage through the k-space center is different.

Herein, the second correction measurement is preferably performed in such a way that the reference sampling pattern describing Cartesian sampling is selected. This means that the recording time window of the reference sampling pattern is ideally selected such that, at a constant amplitude of the measurement gradient pulse relating to a Cartesian direction, the recording times are equidistant and thus, due to the robust selection of the gradient conditions, result in equidistant k-space positions to which the second magnetic resonance signals are to be assigned in the Cartesian direction, for example the x-direction. It is then necessary to differentiate between two cases.

For example, the first correction measurement to be corrected can contain first magnetic resonance signals that were recorded at least partially during a non-constant measurement gradient (relating to the target profile). Then, the present disclosed subject matter expediently provides that, in the case of a measurement sampling pattern describing non-Cartesian sampling, the first magnetic resonance signals are converted to the recording times of the reference sampling pattern before the evaluation of the deviation criterion and/or the alignment. Therefore, gridding is first performed in order to obtain the first magnetic resonance signals with equidistant, i.e., Cartesian, k-space points, meaning that a comparison at the same k-space positions or alignment is meaningfully enabled. This can, for example, take place if the measurement sampling pattern comprises sampling during at least one ramp of the in particular trapezoidal measurement gradient pulse (ramp sampling) and/or the measurement gradient pulse has a sinusoidal shape and/or the measurement gradient pulse is applied for spiral imaging.

In the other case, the first correction measurement to be corrected has been recorded completely during an (assumed) constant measurement gradient. According to the previously discussed embodiment, the second correction measurement (reference measurement) is set up similarly, wherein in particular a larger temporal distance of the recording time window from the beginning of the gradient plateau can be provided. Then, no gridding is required for the initial comparison between the first magnetic resonance signals and the second magnetic resonance signals since the first magnetic resonance signals have already been nominally recorded in equidistant k-space. The alignment for determining the correction function can then be understood as gridding of the first magnetic resonance signals with the second magnetic resonance signals which is performed for best possible agreement in order to determine the correction information.

In general, it can be said that if there is sufficient deviation to justify a correction, the recorded k-spaces of the first correction measurement and the second correction measurement are brought into agreement, wherein a correction function $\Delta k(t)$ is ascertained that describes the deviation of the assumed k-space trajectory $k(t)$ according to the target profile from the real k-space trajectory $k_{real}(t)$ that is actually present:

$$k_{real}(t)=k(t)+\Delta k(t) \quad (3)$$

Herein, the assumed k-space trajectory $k(t)$ is defined by the integral of the assumed target profile of the measurement gradient pulse $G(t)$, $$k(t)=k_0+\gamma \int_{t_0}^{t} G(\tau)d\tau \quad (4)$$

wherein $k_0$ describes the k-space value at the beginning of the recording time window and $t_0$ describes the beginning of the recording time window. Therefore, the magnetic resonance signal in k-space of the first correction measurement to be corrected, $(S_a(k))$, is compared with the magnetic resonance signal of the second correction measurement (reference measurement), $(S_b(k))$, and these are aligned with one another in that the k-space trajectory of the first correction measurement is modified by the correction function $\Delta k(t)$.

Herein, as already mentioned, the ascertaining process in particular takes place before the or an imaging measurement, for example as a preliminary measurement or also as a calibration measurement, in particular during tune-up; this will be discussed in more detail below.

In summary and in general, therefore, the present disclosed subject matter allows consideration and correction of disruptive influences due to imperfect measurement gradient pulses in measurements with ramp sampling or with other non-constant measurement gradients and of imaging measurements that acquire magnetic resonance signals shortly after a ramp of the measurement gradient pulse. This makes it possible to reduce artifacts, for example ghosting artifacts and/or edge elevations and thus to improve image quality.

Compared to known methods from the prior art, for example eddy current compensation by pre-emphasis, the correction proposed here can have a position-specific effect. For example, spatially varying deviations of the electromagnetic field generated by the measurement gradient pulse can be compensated for the recorded slice position in each case. Furthermore, the proposed method can be used as a supplement to the usual eddy current compensation performed by pre-emphasis in order to balance out its limitations. Compared to the use of magnetic field sensors, in particular field probes, no additional sensors and complex integration of the externally measured magnetic field data into the reconstruction is necessary. Therefore, this avoids effort.

In a specific exemplary embodiment, it can, for example, be provided that, if necessary, initially the first magnetic resonance signals are gridded according to the expected target profile using the shape function, i.e., in particular, they are brought to the Cartesian (equidistant) grid defined by the reference sampling pattern in k-space. A comparison is made with the second magnetic resonance signals, which are preferably already present on an equidistant grid in k-space. If there are no deviations or only slight deviations according to the deviation criterion, in particular deviations below a definable threshold, the correction information is ascertained as "no correction necessary". Then, if the deviation criterion was satisfied, the k-spaces are brought into agreement, wherein, for example, initially the k-space center of the first correction measurement and the second correction measurement can be brought into agreement and then the k-space region is successively extended from the k-space center to the left or right until deviations occur in these sections. The determination of the correction function can then, for example, be performed for the various deviating k-space points by increasing or lowering the k-values until agreement is achieved. If this happens for all k-space points of the trajectory section, the result is the new k-space trajectory $k_{real}(t)$ according to equation (3), which takes into account disruptive influences and can be used as preparation for gridding in the imaging measurement (or generally for the assignment of k-space positions to recording times).

As described by formula (3) together with formula (4), the correction function is preferably ascertained in such a way that the shape function representing the real profile results as the sum of the shape function representing the target profile and the correction function. This sum, $k_{real}(t)$, can then, so to speak, be used as a corrected shape function to enable gridding in the correct manner and to reduce artifacts, thereby increasing image quality.

In particular, when an exemplary embodiment relates to ramp sampling, echo planar imaging (EPI) can be used, including for the correction measurements. Herein, it can in particular be provided that an EPI readout train without phase blips is used for the first and the second correction measurement. All echoes, and thus magnetic resonance signals, are consequently recorded in the phase encoding direction (y-direction) in the k-space center, meaning that a lot of signal is present in this respect. Here, in both cases, trapezoidal measurement gradient pulses can be used as measurement gradient pulses, wherein, in the second correction measurement, the second magnetic resonance signals are preferably recorded during the plateau, in particular, as described, after a delay time after the beginning of the plateau.

Herein, the first and the second correction measurement can follow one another directly, in particular also with regard to maintaining the predetermined measurement conditions. In this context, it is particularly expedient for at least one prephasing gradient to be used, meaning that the trajectory section is at least partially swept during the recording time window of the respective sampling pattern in the correction measurements. To enable a comparison and also an adjustment to take place, and this also happens for the relevant region (the trajectory section), it is of course necessary for equal portions of the k-space to be swept in the at least one first and the at least one second correction measurement, in particular in such a way that the entire trajectory section is covered overall. This can be expediently achieved by the prephasing gradient pulses.

Herein, embodiments are conceivable in which the entire trajectory section is sampled in a single first and a single second correction measurement, in particular symmetrically about the k-space center, in such a way that the trajectory section is swept according to the imaging measurement. In many common magnetic resonance sequences for imaging measurements, the gradient moments are selected, including with regard to the prephasing gradients, in such a way that, a region in the outer k-space is recorded at the beginning of the recording time window. In the course of the recording time window, the k-space center is then swept, meaning that the prephasing gradients for the first correction measurement and the second correction measurement can be selected such that dephasing is generated, meaning that the desired outer region of k-space is recorded at the beginning (and at the end) of the recording time window. In this case, in particular, a measurement can take place symmetrically about the k-space center. Therefore, in such exemplary embodiments, the trajectory section is sampled according to the imaging measurement.

However, in particularly preferred exemplary embodiments, it can also be provided that a plurality of first and second correction measurements are performed in which the k-space center is located differently in each case. Then, if the correction function relates to the shape function and thus describes corrections for times of the measurement sampling pattern, it can be provided that a corresponding shift is taken into account when it is ascertained.

In this context, an expedient development of the present disclosed subject matter provides that at least one predetermined time interval is specified in which stronger deviations than in other time sections of the recording time window are expected, wherein in at least one of the at least one first and second correction measurement, the passage through the k-space center is positioned in at least one of the at least one time interval. This can in particular take place by means of a corresponding selection of the prephasing gradient pulses and their dephasing. Herein, it was recognized that the essential factor for the correction described here is that the same portion of the k-space is traversed in the first correction measurement and the second correction measurement, thus enabling comparison and alignment. For example, the prephasing gradient pulses can be selected such that the k-space center is reached in the part of the recording time window of the measurement sampling pattern and the reference sampling pattern that is particularly affected by imperfections in the measurement gradient pulse, for example during one of the gradient ramps or in the temporal vicinity thereof.

This has the advantage that it enables the useable magnetic resonance signal for the calculation of the correction information to be significantly increased. For example, in the example of ramp sampling, the greatest deviations between the target profile and the actual time profile of the measurement gradient pulse occur in the region of the ramps, for which, however, when the k-space center is reached centrally on the plateau of the trapezoidal measurement gradient pulse, the outer k-space region is recorded. Here, due to the strong dephasing in the outer k-space regions, it can happen that the data points that are particularly relevant for the correction contain only few magnetic resonance signals, which is why the correction information can then be strongly influenced by noise effects or, in extreme cases, reliable values can no longer be ascertained. However, if the k-space center is shifted into regions relevant for the correction, the magnetic resonance signal relevant for the determination of the correction information can be significantly increased.

In this context, one expedient development provides that, for each of a plurality of specified time intervals, a pair consisting of the first and second correction measurement is performed such that the passage through the k-space center lies within the respective time interval. Therefore, it can be provided that different pairs of correction measurements are performed in which the k-space center is in each case reached in another region of the recording time windows. For the example of correction in the case of imaging measurements with ramp sampling, this means that a first pair of correction measurements is performed for which the k-space center is reached in temporal proximity or during a first rising gradient ramp of the measurement gradient pulse for the first correction measurement. In a second pair of correction measurements, the k-space center for the first correction measurement is reached in the region of the other ramp in each case, for example a falling ramp.

In such exemplary embodiments, therefore, different, even if possibly at least partially overlapping, k-space regions, which are in particular shifted in relation to the trajectory section in the imaging measurement, are recorded in the different pairs of correction measurements. Herein, it can be provided that, for the different time intervals, due to the respective pair of first and second correction measurements, in each case partial correction functions are ascertained and combined to form the correction function. The recorded k-spaces, wherein a gridding has already been applied for first correction measurements with non-Cartesian sampling, which is based on the shape function of the target profile, are brought into agreement to ascertain the correction function, meaning that respective partial correction functions result. These can be combined to form a common correction function which is composed of the data from the various partial correction functions. Here, provision can be made, for example, for a combination to take place on an overlap of the respective sampled k-space regions by weighted averaging depending on how far away from the k-space center the underlying magnetic resonance signals were recorded. It should be noted at this point, that, on the one hand, of course the time shifts caused by the shifts of the k-space centers should be taken into account and, on the other hand, the time intervals do not necessarily have to cover the entire trajectory section if it can be said with sufficient certainty for a section of the trajectory section that no strong deviations are expected here. Then, the correction function for sections that are not covered by time intervals can, for example, be set to zero. However, it is also conceivable that the entire recording time window be divided into time intervals, therefore covered completely, and, so to speak, measured precisely in successive sections.

In this context, it should also be noted in general that, in the case of a plurality of pairs of first and second correction measurement, the magnetic resonance signals and/or partial correction functions of pairs can in any case preferably be statistically combined resulting in an increase in the signal-to-noise ratio. In other words, it can be provided that, in order to achieve a higher signal-to-noise ratio, the first and the second correction measurement can also be repeated, in particular within the echo train, wherein processing can then take place based on the averaged magnetic resonance signals or averaging of the processing result, for example partial correction information. A statistical combination, in particular averaging and/or joint optimization, can also take place in relation to recordings of the first and second magnetic resonance signals from a plurality of coil channels and/or slices. If slice-specific differences are to be expected, for example, since field interference induced by eddy currents changes in the slice direction, it is expedient to treat different slices, i.e., ascertain slice-specific correction information, separately.

Basically and figuratively speaking, herein it can be said that, in order to align the magnetic resonance signals based on the shape function corresponding to the assumed target profile, k-space points are shifted to the matching values of the second magnetic resonance signals, wherein the shift corresponds to the corresponding correction to be made. However, this preferably takes place with regard to minimizing the overall deviation, i.e., for all (deviating) k-space points.

Therefore, a particularly preferable embodiment of the present disclosed subject matter provides that the alignment takes place in an optimization method relating to parameters of the correction function, wherein the optimization method minimizes the distances between the first and the second magnetic resonance signals. Herein, minimization of the distances in both k-space and image space is conceivable, wherein corresponding, basically known, distance measures can be used. The recorded k-spaces, specifically the profiles of the magnetic resonance signals in k-space, are therefore brought into agreement by an optimization method in that the correction function $\Delta k(t)$ is determined. Herein, the optimization method used can, for example, be simulated cooling and/or a Frank-Wolfe method and/or the optimization can take place by means of a trained artificial intelligence function, for example using a correspondingly trained neural network. Simulated cooling is a probabilistic technique for approximating the global optimum. The Frank-Wolfe algorithm is a first-order iterative optimization algorithm for constrained convex optimization. Both these variants have been found to be particularly suitable; however, of course it is also possible to use other optimization algorithms and approaches during the course of the present disclosed subject matter.

In an expedient development of the present disclosed subject matter, it can be provided that, if the measurement gradient pulse is used with opposite polarities during the readout process in the imaging measurement, correction information is ascertained for both polarities. For example, in the case of EPI magnetic resonance sequences, measurements are performed with alternating polarities of the measurement gradient pulse. While it is in principle conceivable to further use the results for one measurement gradient pulse for the opposite polarity as well, it is particularly advantageous for the correction information for positive and negative gradient shapes of the measurement gradient pulse to be treated separately. This enables non-linear disruptive influences that affect the polarities differently to be corrected.

As already explained, it can furthermore be provided that the correction information is determined separately for different slices. This is in particular expedient if disruptive influences, for example field interference induced by eddy currents, change in the slice direction.

In a preferred first variant of the disclosed subject matter, it can be provided that the ascertaining process takes place as a preliminary measurement before a subsequent imaging measurement when the object to be recorded has already been positioned and the correction information is ascertained specifically for the imaging measurement. The proposed ascertaining of the correction information can therefore take place the form of a "pre-scan" before each imaging measurement for which it is to be applied, for example before each EPI measurement with ramp sampling. The advantage of this first variant of the disclosed subject matter is that the correction is up-to-date and examination-specific. Herein, a particularly preferable embodiment of this first variant provides that the ascertaining process takes place during the course of a phase correction measurement for Nyquist ghost correction in such a way that the magnetic resonance signals are used both to ascertain the correction information and for phase correction. This enables the ascertaining process to be performed in a time-neutral manner after an external phase correction scan has been correspondingly modified. To date, with such phase correction measurements, for Nyquist ghost correction, it is usual to record three uncoded k-space lines at the time of the echo center in the later imaging measurement. At least one of the correction measurements, which in any case, as already discussed, can generally preferably take place uncoded in the phase encoding direction, can be supplemented accordingly by at least one further partial measurement, meaning that the necessary phase correction data is also completely available and a combination of both correction methods is achieved. For example, if both polarities of the measurement gradient pulse and the gradient conditions are measured, and thus two k-space lines are recorded in any case, further output of the measurement gradient pulse can be added to one of the polarities thus enabling averaging of the results before and after the other polarity for phase correction.

In a second variant of the disclosed subject matter, however, it is also conceivable for the ascertaining process to be performed during the course of a calibration process for the magnetic resonance facility used, in particular during a tune-up measurement. Herein, it is particularly expedient for correction information to be ascertained for different spatial directions and/or types of imaging measurements by ascertaining processes and/or interpolation between correction information of different ascertaining processes. For example, it is possible for account to be taken of all later possible imaging variants, wherein, as mentioned, interpolation between different correction information, in particular for different k-space trajectory sections, is also possible. Particularly advantageously, a phantom can be used for the correction measurements, wherein at least one property of the phantom is taken into account when ascertaining the correction function. Therefore, the calibration can take place with a defined phantom and corresponding prior knowledge of image or k-space content. A further advantage of this variant is that, due to the lower time criticality during tune-up, the correction measurements can be repeated several times, thus enabling statistical combinations, for example averaging, and a correspondingly higher signal-to-noise ratio relating to the magnetic resonance signals and the correction information can be achieved.

Herein, it should be noted in general that of course the procedure according to the disclosed subject matter is generally also applicable to a plurality of measurement gradient pulses that are at least temporarily applied simultaneously and relate to different directions in k-space, in particular therefore with regard to two-dimensional or even three-dimensional trajectory sections. However, in this case, more complex, because it has more dimensions, optimization may be necessary.

In principle, in particular when performing the ascertaining process during the course of a tune-up, optimization with k-spaces that are phase-encoded in the $k_y$-direction is also conceivable. This means correction measurements can be performed in which, for example, by means of blipping gradient pulses, k-space lines positioned differently in the phase encoding direction can be sampled as trajectory sections, for example one to forty parallel k-space lines in the $k_x$-direction which are offset in the $k_y$-direction. This is particularly advantageous during the course of a tune-up measurement with a phantom with known properties, since lower signal strength outside the k-space center can then be compensated based on prior knowledge.

Herein, for example, recording in two echo trains and/or suitable interleaving of the k-space lines can take place in order to establish optimal comparability for the first and the second correction measurement, and it should be taken into account that the bandwidth in the phase encoding direction is identical for both recordings in order to avoid spatial distortions. In addition to interleaving, it is then conceivable to record with reduced resolution or to use a partial Fourier technique for the second Cartesian sampling correction measurement.

Herein, it should be noted once again that the procedure according to the disclosed subject matter can of course also be additionally implemented for further measures for correcting interference effects in order to compensate limitations thereof. For example, it can, for example, be provided that during the ascertaining and use of the correction information, at least one further measure is performed for the correction of interference effects with regard to the shape of the measurement gradient pulse, in particular output of correction gradient pulses for eddy current compensation (pre-emphasis). In this way, therefore, remaining deviations are measured and corresponding correction information is determined in the ascertaining process according to the disclosed subject matter.

In addition to the method, the present disclosed subject matter also relates to a magnetic resonance facility having a control facility embodied to perform the method according to the disclosed subject matter. All explanations relating to the method according to the disclosed subject matter can be applied analogously to the magnetic resonance facility according to the disclosed subject matter, meaning that the aforementioned advantages can also be achieved therewith.

Therefore, in addition to the main magnet, the magnetic resonance facility also has in particular a gradient coil array and a radio-frequency coil array which can be actuated appropriately by means of the control facility in recording mode. For this purpose, the control facility can in particular have a sequence unit for controlling the recording mode of the magnetic resonance facility, in particular also for actuating the gradient coil array for outputting gradient pulses and for actuating a receiving facility for recording magnetic resonance signals. In particular, therefore, the sequence unit can be embodied to perform the first and the second correction measurement. The control facility can furthermore comprise a correction unit for ascertaining the correction information. Further functional units of the control facility, generally speaking, having at least one processor and one storage medium are of course possible for further conceivable steps of the method according to the disclosed subject matter.

A computer program according to the disclosed subject matter can be loaded directly into a control facility of a magnetic resonance facility and configures the latter to perform the steps of a method according to the disclosed subject matter when the computer program is executed. The computer program can be stored on an electronically readable data carrier according to the disclosed subject matter, which therefore comprises control information stored thereon that comprises at least one computer program according to the disclosed subject matter and, when the data carrier is used in a control facility of a magnetic resonance facility causes the latter to perform the method according to the disclosed subject matter. The electronically readable data carrier can in particular be a non-transient data carrier, for example a CD-ROM.

BRIEF DESCRIPTION OF THE DRAWINGS

Further advantages and details of the present disclosed subject matter will be apparent from the exemplary embodiments described in the following and from the drawing, in which:

FIG. 7 shows a magnetic resonance facility according to the disclosed subject matter, and FIG. 8 shows the functional structure of a control facility of the magnetic resonance facility.

DETAILED DESCRIPTION

The following describes an exemplary embodiment of the present disclosed subject matter which is applied in the case of ramp sampling for acceleration in echo planar imaging (EPI). Nevertheless, the correction approach according to the disclosed subject matter can of course be applied to all cases in which the gradient shape of at least one measurement gradient pulse deviates from a temporal target profile in reality, meaning that what has been outlined here can for example also be applied to the use of sinusoidal measurement gradient pulses and spiral imaging and also to standard Cartesian imaging if there are deviations from the constant plateau shape usually used.

Figure 1:
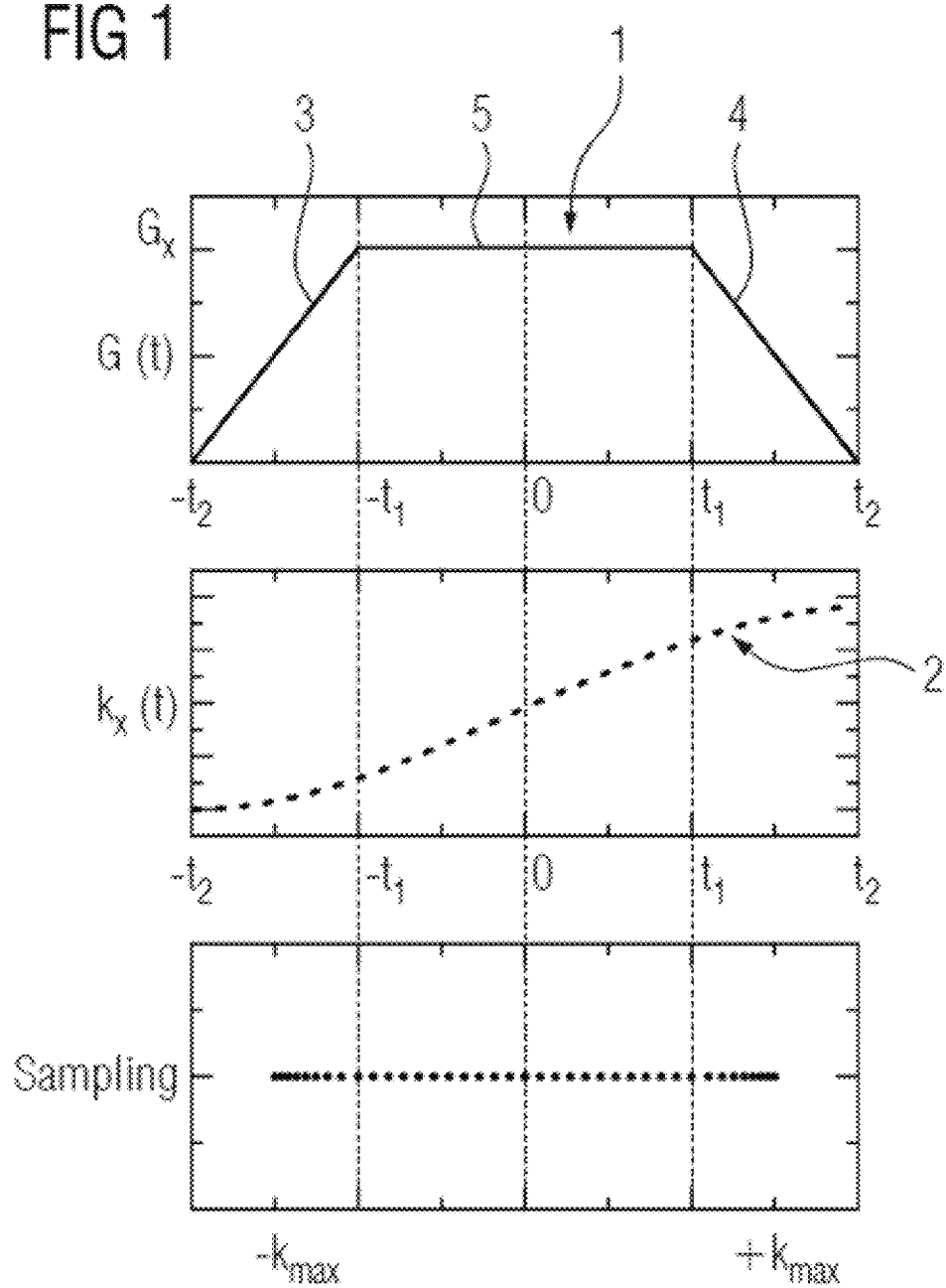
FIG. 1 shows graphs explaining a ramp sampling technique.

FIG. 1 explains ramp sampling in the form of a number of graphs. A trapezoidal target profile 1, referred to as G(t), is used as the target profile 1 of the measurement gradient pulse, cf. the upper partial image and formula (1). Herein, the x-direction is considered to be the readout direction resulting in a k-space-trajectory section 2 in the $k_x$-direction. If now a measurement sampling pattern is used with a recording time window that also provides temporally equidistant recording times along the ramps 3, 4 of the trapezoidal target profile 1, according to the lowest graph in FIG. 1, this results in a higher sampling density in the time range of the ramps 3, 4 and Cartesian sampling, i.e., equidistant sampling in k-space in the $k_x$-direction, only in the region of the plateau 5.

Therefore, a shape function, such as, for example described by equation (1) is used to calculate which k-space position is assigned to which recording time, meaning that the recorded magnetic resonance signals can be calculated back onto a Cartesian sampling grid by means of gridding. If the target profile according to equation (1) is assumed, the k-space positions can be ascertained by equation (2), cf. middle graph. The corresponding required parameters can be derived from the magnetic resonance sequence used for the imaging measurement and are available in the control facility of the magnetic resonance facility.

Herein, if, as described so far, the target profile 1 is assumed to be actually present, there is always a source of error if the actual gradient shape, i.e., the actual profile, deviates from the target profile 1 due to time delays, not entirely compensated eddy currents and the like. Such a case is shown schematically in FIG. 2 where in turn the target profile 1 is depicted as an ideal shape together with an exemplary real time profile 6 deviating therefrom, wherein deviations can in particular be identified in the region of the ramps 3, 4 and at the beginning of the plateau 5. If the target profile 1 is now further assumed, image artifacts can occur.

Figure 3:
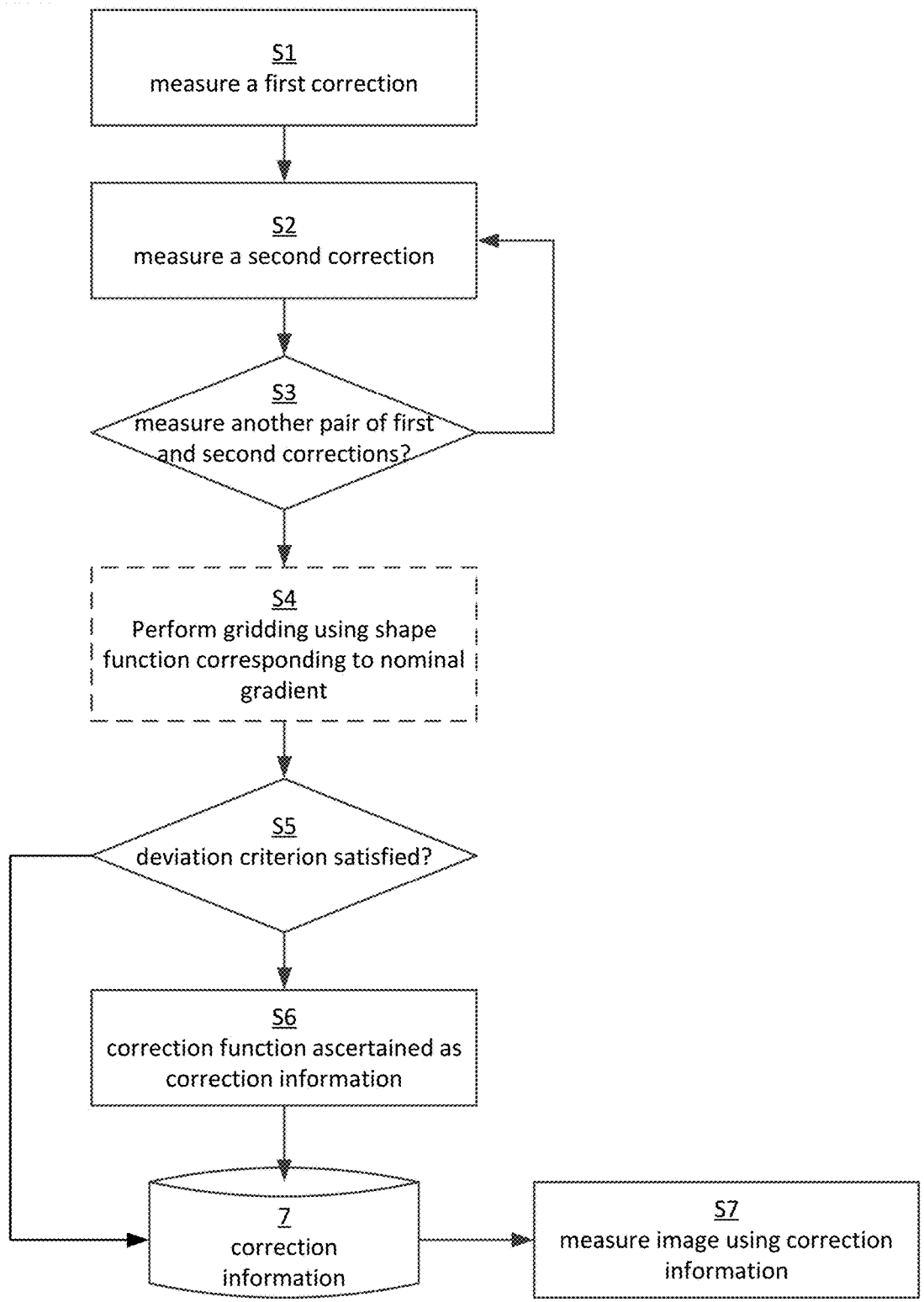
FIG. 3 shows a flow chart of an exemplary embodiment of the method according to the disclosed subject matter.

The exemplary embodiment of the method according to the disclosed subject matter depicted with reference to FIG. 3 is now intended to ascertain this actual time profile 6 of the measurement gradient pulse. For this purpose, it is assumed that the real trajectory in k-space, $k_{real}(t)$, can be written according to formula (3) as the sum of the profile k(t) derived from the target profile and a correction function Δk(t), wherein in Δk(t) is to be ascertained in the course of an ascertaining process.

Herein, this ascertaining process, described in FIG. 3 by steps S1 to S6, can already be carried out either as part of a tune-up, i.e., a calibration process of the magnetic resonance facility, meaning that correction information 7 ascertained can be used for a large number of subsequent imaging measurements, or preferably as a preliminary measurement (pre-scan) of at least one actual imaging measurement. Herein, in the former case, correction information 7 should be provided for all conceivable imaging measurements, in particular therefore magnetic resonance sequences, different gradient directions and/or possibly other different parameters, wherein here the ascertaining process is not time-critical.

In the case of a preliminary measurement, in return, advantageously also current effects and possibly even influences of the object to be recorded can also be mapped and corrected. Here, the ascertaining process is preferably performed during the course of a phase correction measurement for Nyquist ghost correction in such a way that the magnetic resonance signals can be used both to ascertain the correction information and for phase correction. Herein, for example, the sequence of the first and/or second correction measurement, which is still to be described is supplemented by at least one further gradient playout and thus k-space line recording, meaning that the three k-space line recordings required in this context are available. For example, when measuring both polarities of a measurement gradient pulse in the same echo in the first correction measurement, it is easily possible, for example, to put a further output of the negative polarity first.

In both variants, i.e., both during the tune-up-measurement and during the course of a preliminary measurement, the correction information can also be determined slice-specifically in order, for example, to map only locally present effects in the correction information.

According to steps S1 and S2, in each case a first correction measurement is performed to record first magnetic resonance signals and a second correction measurement is performed to record second magnetic resonance signals. Herein, in the first correction measurement, the measurement sampling pattern, which is also used in the imaging measurement with the measurement gradient pulse whose shape could deviate, is applied to the measurement gradient pulse under predetermined conditions. This means that the recording time window and the recording times lie with respect to the measurement gradient pulses as they would lie in a corresponding imaging measurement, wherein this, as will be explained in more detail, this does not necessarily have to applied with regard to the rephasing. This means that the k-space region sampled by the measurement sampling pattern does not necessarily have to correspond, in particular in relation to position, to the trajectory section that is intended to take place in the imaging measurement by means of the measurement sampling pattern. The result of the first correction measurements are first magnetic resonance signals covering at least part of the trajectory section of a corresponding imaging measurement.

Figure 2:
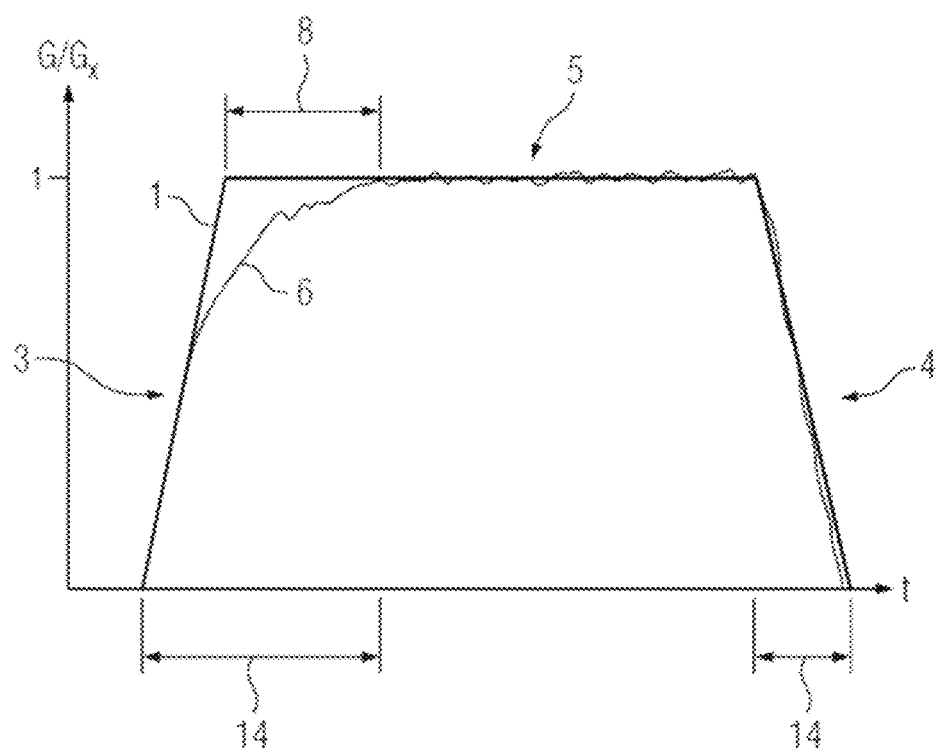
FIG. 2 shows a comparison of a real time profile of a measurement gradient pulse with a target profile of the measurement gradient pulse.

In the second correction measurement in step S2, second magnetic resonance signals are recorded for the same k-space region and with the same predetermined measurement conditions, but using a reference sampling pattern—for sampling the same k-space region—at other gradient conditions, which can be brought about either by the measurement gradient pulse, but equally well by a reference gradient pulse. For the changed gradient conditions, fewer deviations from an assigned reference target profile are expected than deviations of the actual time profile 6 from the target profile 1 of the measurement gradient pulse. In the present case, the gradient conditions for the second correction measurement provide for measurement during a plateau of a trapezoidal gradient pulse (of the measurement gradient pulse or a reference gradient pulse), wherein the reference sampling pattern provides for Cartesian, i.e., equidistant, sampling of the k-space region that has already been sampled by the first correction measurement. The prephasing gradient pulses are also selected accordingly. Herein, in the present case, particularly advantageously, the recording time window of the reference sampling pattern is not started immediately at the beginning of the gradient plateau 5, since, as FIG. 2 shows by way of example, initially there may be even stronger deviations from the constant gradient amplitude, $G_x$. Therefore, there is a wait for a delay time 8, which is also shown in FIG. 2, before starting with the recording time window of the reference sampling pattern. In the delay time 8, disturbance effects, in particular eddy current effects with short time constants, have already sufficiently decayed. The delay time 8 can, for example, be 100 to 500 μs.

Therefore, in the second correction measurement in step S2, second magnetic resonance signals of the same k-space region as in the first correction measurement are recorded; this is ensured by prephasing gradients and the reference sampling pattern, but under changed more robust gradient conditions, in which deviations are significantly smaller or not measurable. Cartesian sampling takes place.

At this point, it should also be noted with regard to the predetermined measurement conditions that preferably a phantom with known properties is used for an ascertaining process in tune-up, meaning that, therefore, information relating to this can also be included in the ascertaining of the correction information 7. In the case of a preliminary measurement before an imaging measurement, the object to be recorded, for example a patient, is ideally already positioned for the imaging measurement, meaning that the conditions that also apply for the following imaging measurement are present.

Figure 4:
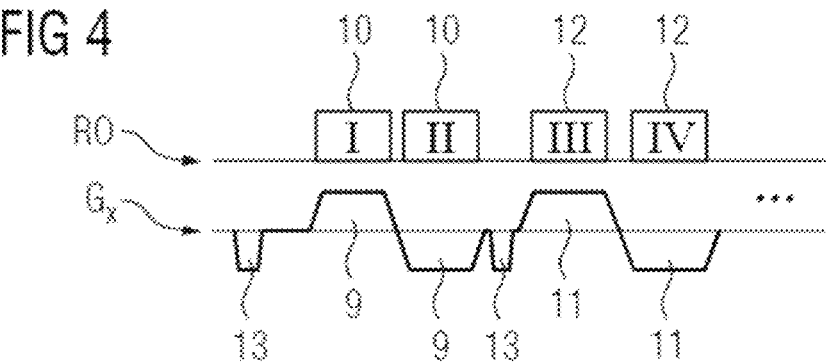
FIG. 4 shows a section from a sequence diagram for performing correction measurements.

The relevant portions of a sequence diagram for such correction measurements, which take place there immediately one after the other, are shown in FIG. 4. Herein, in the present case, measurements in the phase encoding direction ($k_y$) are made in the k-space center or uncoded. It should be noted that, especially during the course of a tune-up measurement with a known phantom, phase encoding, can, for example, also take place by using blips and prior knowledge about the phantom can be included.

As shown in FIG. 4, the measurement gradient pulse 9 is used in both conceivable polarities one after the other, wherein, for each polarity in recording time windows 10 of the first correction measurement, first magnetic resonance signals are recorded, here marked as recording processes I and II. In combination with a phase correction scan, to record three k-space lines, a further output of the measurement gradient pulse 9 in negative polarity can be put first and provided with another recording time window 10, meaning that averaging of the preceding recording time window 10 (data recording zero) and the results of the data recording II enable the information required for the phase correction with regard to Nyquist ghosts to be obtained.

The reference gradient pulse 11, which is also trapezoidal here, is also output in both polarities, wherein second magnetic resonance signals are also recorded for both polarities in corresponding recording time windows 12 of the reference sampling pattern in the second correction measurement, here marked III and IV. As can be seen, the recording time windows 10 of the measurement sampling pattern also comprise ramps 3, 4 of the measurement gradient pulse 9, while the recording time windows 12 of the reference sampling pattern start after the delay time 8 of the gradient plateau 5 of the reference gradient pulse 11 and only extend over this. FIG. 4 also shows the prephasing gradient pulses 13 via which it is set that the same k-space region is sampled and of course how it lies.

Figure 5:
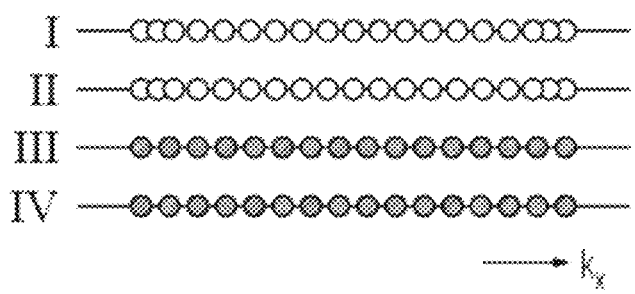
FIG. 5 shows a sampling profile for the sequence diagram in FIG. 4.

Herein, FIG. 5 shows the resulting sampling densities in k-space for the recording time windows 10, 12 numbered I, II, III and IV.

To return to FIG. 3, step S3 represents a check as to whether further pairs consisting of the first and second correction measurement (steps S1 and S2) should be performed. This can be expedient for a plurality of different reasons, which can also be combined. In particular if there is no time criticality, the same first and second correction measurements can be repeated several times in order then to be able to statistically average and, for example, improve the signal-to-noise ratio. It is also possible to measure different slices and/or gradient directions and/or different magnetic resonance sequences (measurement gradient pulses and measurement sampling patterns) one after the other, i.e., before evaluation.

However, in the present case, several different pairs of first and second correction measurements are also carried out, which refer to different positions of the k-space center. Thus, it can be recognized from FIG. 2 that the recording period 10 includes time intervals 14 in the time profiles 1, 6 in which particularly large deviations are present or expected. In FIG. 2, these are the time interval 14 of the rising ramp 3 and the delay time 8 (which can also be divided into two time intervals 14) and the time interval 14 of the falling ramp 4. If a usual recording were now made along the trajectory section 2, the k-space center (and thus the greatest signal strength) would be located more or less centrally in the plateau 5, while in the area of the ramps 3, 4, outer areas of the k-space would be measured in which little signal is present. However, it is precisely here that a lot of signal would be desirable, since this is where strong deviations are expected and a correction is to be determined in the form of the correction function.

Therefore, in the present exemplary embodiment, the first and the second correction measurements are each performed once for each time interval and, to be precise, in such a way that the passage through the k-space center comes to lie in the respective time interval 14, i.e., once with the k-space center in the regions of the rising ramp 3/delay time 8 and once in the region of the falling ramp 4, in particular within the respective time windows 14. In this way, high-quality data with high signal strength is obtained where it is most necessary for the correction.

Step S4, shown as optional, is only not required if the measurement sampling pattern and the reference sampling pattern each aim at Cartesian sampling of the k-space. In the example of ramp sampling shown here, this is of course not the case, as FIG. 5 shows. Therefore, here, in a step S4, as in other applications (for example sinusoidal gradients and/or spiral sampling), gridding is performed using the shape function corresponding to the nominal gradient 1, cf. for example equations (1) and (2). This means, that, for each recording time point in the recording time window 10, the k-space position to which the magnetic resonance signal measured at that recording time point should be assigned is established using the shape function corresponding to the target profile 1. Thereafter, gridding takes place on the Cartesian sampling grid of the reference sampling pattern thus providing assigned values of the magnetic resonance signals for all recording times of the reference sampling pattern.

In step S5, a deviation criterion is checked on this basis, which is satisfied if the deviations between the first and second magnetic resonance signals exceed a threshold value. If the deviation criterion is not satisfied in step S5, the correction information 7 is determined as "no correction necessary". However, if it is satisfied, in a step S6, the correction function Δk(t) is ascertained as correction information 7 by aligning the first and second magnetic resonance signals in k-space to one another. Herein, with regard to the different pairs of first and second correction measurements for different time intervals 14, it should be noted that, on the one hand, it is conceivable to combine the respective first and second magnetic resonance signals statistically, for example by weighted averaging, for the k-space region covered by the trajectory section 2 overall (taking into account the time shift with regard to the k-space center); however, it is also possible to determine partial correction functions and then to combine them statistically, which is what happens in the present case.

Figure 6:
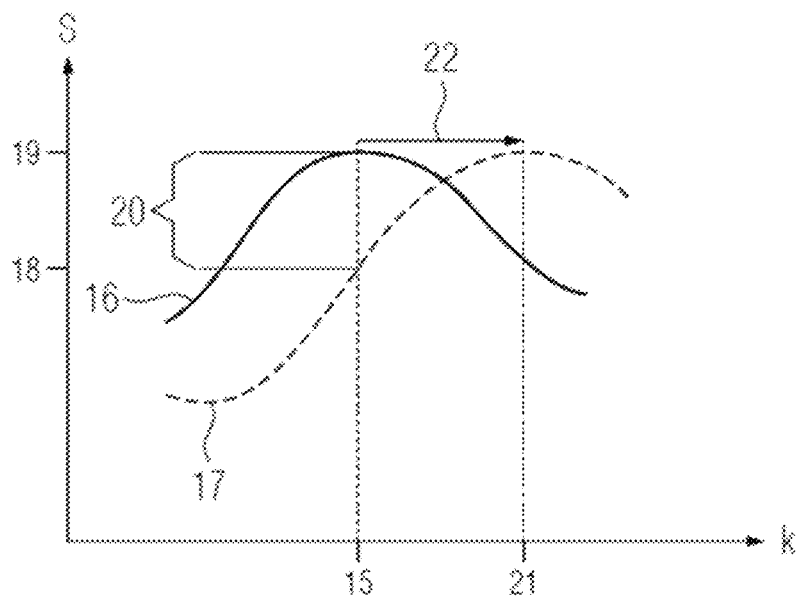
FIG. 6 shows a sketch describing the deviation and alignment between the k-spaces.

FIG. 6 explains the alignment process in the form of a schematic sketch, wherein a k-space position 15 assigned to a recording time of the reference scanning pattern is schematically shown in a local environment with the profiles of the first magnetic resonance signals 16 and the second magnetic resonance signals 17. It is evident that different values 18, 19 for the magnetic resonance signals 17, 16 result for the k-space position 15 assigned to the recording time, meaning that of course there is a deviation 20, which was checked in the deviation criterion of step S5.

The cause of the deviation 20 is the deviation of the actual time profile 6 of the measuring gradient pulse 9 from the nominal profile 1, which is why the conversion with the shape function and the gridding have resulted in the higher value 19. To determine the correction function Δk(t), it is now necessary to determine the k-space position 21 to which the value 19 actually belongs, here, depicted by a shift according to arrow 22. While it would in principle be conceivable to ultimately align the first magnetic resonance signals 16 and second magnetic resonance signals 17 to each other point by point by means of such shifts, for example by checking for each of the points, starting at the k-space center, where it would have to be shifted, preferred exemplary embodiments, such as that shown in FIG. 3, provide for the use of optimization methods that select the parameters of the correction function Δk(t) such that the distance between the profiles of the magnetic resonance signals 16, 17 is minimized. In other words, the recorded k-spaces are brought into agreement by the optimization procedure in that the correction function Δk(t) is determined. For example, optimization methods such as simulated cooling, a Frank-Wolfe method, and the like can be used here; an appropriately trained neural network can also be used. Here, the difference between the first and second magnetic resonance signals is minimized.

In the present case, after the prephasing gradients 13 have been selected for the respective time intervals 14 in such a way that the k-space center is reached in the respective time intervals 14, in the present case a common correction function Δk(t) is determined which is composed of the data from the different corrections. For example, individual partial correction functions of the different pairs of correction measurements can be determined first and then combined by suitable methods, for example by weighted averaging. Of course, the time shift due to the displacement of the k-space center with respect to the actual imaging measurement should be taken into account.

Herein, it should be noted at this point that, although the deviation 20 in FIG. 6 was shown by example in k-space, of course, comparisons or the determination of distance measures can also be carried out in image space, since a Fourier transform can easily be carried out without any gridding onto the Cartesian sampling grid.

In the present example, as depicted, correction information 7 is in each case ascertained separately for each of the different polarities of the measuring gradient pulse 9, meaning that nonlinear disruptive influences acting differently on the two polarities can be corrected.

To return to FIG. 3, in a step S7, the determined correction information 7 can then be used for at least one imaging measurement, wherein, if the correction information 7 contains correction information determined in step S6, the target shape function based on the target trajectory 1 and the correction function are added together to form the shape function to ascertain the k-space positions for the magnetic resonance signals at the recording times of the measurement sampling pattern. After that, as is known, gridding onto a Cartesian grid can take place.

FIG. 7 shows a schematic sketch of a magnetic resonance device 23 according to the disclosed subject matter, which, as is known in principle, comprises a main magnet unit 24 which defines a cylindrical patient receptacle 25 into which a patient can be inserted by means of a patient bench, not shown in more detail here. The patient receptacle is surrounded by a high-frequency coil arrangement, not shown in more detail here, and a gradient coil arrangement 26, by means of which the afore-discussed types of gradient pulses can be generated.

The operation of the magnetic resonance device 23 is controlled by a control device 27 which is designed to perform the method according to the disclosed subject matter.

FIG. 8 shows the functional structure of the control device 27, which comprises at least one processor and at least one memory medium 28, in more detail. In particular, first and second magnetic resonance signals 16, 17 of the correction measurements and correction information 7 can also be stored in the memory medium 28.

As is known in principle, the control device 27 comprises a sequence unit 29, via which the recording operation of the magnetic resonance device 23 is controlled, in particular therefore also the first and the second correction measurement in steps S1 and S2 and the imaging measurement in step S7. In a correction unit 30, the deviation criterion according to step S5 can be checked and, if necessary, the correction function according to step S6 can be determined. The correction unit 30 provides the correction information 7 accordingly. For performing step S4, the control device 27 may also comprise a gridding unit 31. Of course, further functional units are also conceivable, for example with regard to further tune-up measurements, phase correction from a preliminary measurement and the like.

Although the disclosed subject matter has been described in greater detail by the preferred exemplary embodiment, the disclosed subject matter is not restricted by the disclosed examples and other variations can be derived herefrom by the person skilled in the art without departing from the scope of protection of the disclosure.

The invention claimed is:

1. A method for operating a magnetic resonance device in which a measurement gradient pulse is used to record magnetic resonance signals for sampling k-space along a trajectory section, wherein the measurement of the magnetic resonance signals takes place at recording times forming a measurement sampling pattern in a recording time window during the measurement gradient pulse and a shape function describing a time profile of the measurement gradient pulse is used to assign magnetic resonance signals to k-space points, wherein, in order to ascertain correction information relating to deviations of a real time profile of the measurement gradient pulse from an assumed target profile of the measurement gradient pulse in the recording time window to be used in an imaging measurement during an ascertaining process, the method comprises:

the magnetic resonance device measuring a first correction to ascertain first magnetic resonance signals of the trajectory section by applying the measurement sampling pattern to the measurement gradient pulse under predetermined measurement conditions;

the magnetic resonance device measuring a second correction to ascertain second magnetic resonance signals of the trajectory section under the predetermined measurement conditions using a reference sampling pattern at gradient conditions of the measurement gradient pulse and/or a reference gradient pulse for which fewer deviations from an assigned reference target profile are expected; and when a deviation criterion comparing the first and second magnetic resonance signals is satisfied, a correction unit of a control device of the magnetic resonance device ascertaining a correction function for the shape function as correction information by aligning the first and the second magnetic resonance signals to one another to improve a quality of magnetic resonance image data produced by the magnetic resonance device.

2. A magnetic resonance device comprising:

a control device operable to perform a method for operating a magnetic resonance device in which a measurement gradient pulse is used to record magnetic resonance signals for sampling k-space along a trajectory section, wherein the measurement of the magnetic resonance signals takes place at recording times forming a measurement sampling pattern in a recording time window during the measurement gradient pulse and a shape function describing a time profile of the measurement gradient pulse is used to assign magnetic resonance signals to k-space points, wherein, in order to ascertain correction information relating to deviations of a real time profile of the measurement gradient pulse from an assumed target profile of the measurement gradient pulse in the recording time window to be used in an imaging measurement during an ascertaining process, wherein the magnetic resonance device is operable to measure a first correction to ascertain first magnetic resonance signals of the trajectory section by applying the measurement sampling pattern to the measurement gradient pulse under predetermined measurement conditions, and wherein the magnetic resonance device is operable to measure a second correction to ascertain second magnetic resonance signals of the trajectory section under the predetermined measurement conditions using a reference sampling pattern at gradient conditions of the measurement gradient pulse and/or a reference gradient pulse for which fewer deviations from an assigned reference target profile are expected; and a correction unit operable to, when a deviation criterion comparing the first and second magnetic resonance signals is satisfied, ascertain a correction function for the shape function as correction information by aligning the first and the second magnetic resonance signals to one another to improve a quality of magnetic resonance image data produced by the magnetic resonance device.

3. A non-transitory electronically readable data carrier on which a computer program is stored, and when executed on a control device of a magnetic resonance device, performs a method for operating a magnetic resonance device in which a measurement gradient pulse is used to record magnetic resonance signals for sampling k-space along a trajectory section, wherein the measurement of the magnetic resonance signals takes place at recording times forming a measurement sampling pattern in a recording time window during the measurement gradient pulse and a shape function describing a time profile of the measurement gradient pulse is used to assign magnetic resonance signals to k-space points, wherein, in order to ascertain correction information relating to deviations of a real time profile of the measurement gradient pulse from an assumed target profile of the measurement gradient pulse in the recording time window to be used in an imaging measurement during an ascertaining process, the method comprises:

measuring a first correction to ascertain first magnetic resonance signals of the trajectory section by applying the measurement sampling pattern to the measurement gradient pulse under predetermined measurement conditions;

measuring a second correction to ascertain second magnetic resonance signals of the trajectory section under the predetermined measurement conditions using a reference sampling pattern at gradient conditions of the measurement gradient pulse and/or a reference gradient pulse for which fewer deviations from an assigned reference target profile are expected; and when a deviation criterion comparing the first and second magnetic resonance signals is satisfied, ascertaining a correction function for the shape function as correction information by aligning the first and the second magnetic resonance signals to one another to improve a quality of magnetic resonance image data produced by the magnetic resonance device.

4. The method as claimed in claim 1, wherein the recording time window of the reference sampling pattern lies entirely within a gradient plateau, and spaced apart from a beginning of the gradient plateau by at least one predetermined delay time.

5. The method as claimed in claim 1, further comprising:
selecting the reference sampling pattern describing Cartesian sampling.

6. The method as claimed in claim 5, wherein, in case of a measurement sampling pattern describing non-Cartesian sampling, the method comprises:
converting the first magnetic resonance signals to the recording times of the reference sampling pattern before an evaluation of the deviation criterion and/or the alignment.

7. The method as claimed in claim 1, wherein the measurement sampling pattern comprises sampling during at least one ramp of a trapezoidal measurement gradient pulse and/or at a beginning of a plateau of the trapezoidal measurement gradient pulse and/or the measurement gradient pulse has a sinusoidal shape and/or the measurement gradient pulse is applied for spiral imaging.

8. The method as claimed in claim 1, wherein the first and the second correction measurement follow one another directly and/or at least one prephasing gradient pulse (13) is used, meaning that the trajectory section is at least partially swept during the recording time window (10, 12) of the respective sampling pattern in the correction measurements.

9. The method as claimed in claim 1, further comprising:
specifying at least one predetermined time interval, in which stronger deviations than in other time sections of the recording time window are expected, wherein, in at least one of the at least one first and second correction measurement, passage through a k-space center is positioned in at least one of the at least one predetermined time interval.

10. The method as claimed in claim 9, wherein, for each of a plurality of specified time intervals, a pair consisting of the first and second correction measurement is performed such that passage through a k-space center lies within the respective time interval, wherein, based on the respective pair, in each case partial correction functions are ascertained for different time intervals and combined to form the correction function.

11. The method as claimed in claim 1, wherein, in order to align the magnetic resonance signals, k-space points of the first magnetic resonance signals ascertained based on the shape function corresponding to the assumed target profile are shifted to matching values of the second magnetic resonance signals, wherein a shift corresponds to a corresponding correction to be made.

12. The method as claimed in claim 1, wherein the alignment takes place in an optimization method relating to parameters of the correction function that minimizes distances between the first and the second magnetic resonance signals.

13. The method as claimed in claim 1, wherein the ascertaining process takes place as a preliminary measurement before a subsequent imaging measurement when an object to be recorded has already been positioned and the correction information is ascertained specifically for the imaging measurement.

14. The method as claimed in claim 13, wherein the ascertaining process takes place during a phase correction measurement for Nyquist ghost correction such that the magnetic resonance signals are used both to ascertain the correction information and for phase correction.

15. The method as claimed in claim 1, wherein the ascertaining process is performed during a tune-up measurement during a calibration process for the magnetic resonance device used.

16. The method as claimed in claim 15, wherein correction information is ascertained for different spatial directions and/or types of imaging measurements by ascertaining processes and/or interpolation between correction information from different ascertaining processes and/or a phantom is used for the correction measurements, wherein at least one property of the phantom is taken into account when ascertaining the correction function.

* * * * *